United States Patent [19]

Böhshar et al.

[11] Patent Number: 5,109,043
[45] Date of Patent: Apr. 28, 1992

[54] PROCESS FOR THE PREPARATION OF ORGANOPHOSPHORUS DERIVATIVES OF 2,4-DI-TERT-BUTYLPHENOL, OF 4,4'-DIHALOMAGNESIUM COMPOUNDS OF BIPHENYL AND THE USE OF THE ORGANOPHOSPHORUS DERIVATIVES FOR THE STABILIZATION OF POLYOLEFIN MOLDING

[75] Inventors: Manfred Böhshar, Kelkheim/Taunus; Hans-Jerg Kleiner, Kronberg/Taunus; Karl Waldmann, Bad Soden am Taunus; Gerhard Pfahler, Augsburg, all of Fed. Rep. of Germany

[73] Assignee: Hoechst Aktiengesellschaft, Frankfurt am Main, Fed. Rep. of Germany

[21] Appl. No.: 452,751

[22] Filed: Dec. 19, 1989

[30] Foreign Application Priority Data

Dec. 21, 1988 [DE] Fed. Rep. of Germany ....... 3843016
Mar. 1, 1989 [DE] Fed. Rep. of Germany ....... 3906435

[51] Int. Cl.⁵ .................. C07B 49/00; C07F 9/48; C08K 5/5333
[52] U.S. Cl. .................. 524/126; 260/665 G; 558/134; 558/144; 558/156
[58] Field of Search .......... 558/144, 156, 134; 524/125, 126; 260/665 G

[56] References Cited

U.S. PATENT DOCUMENTS

| | | | |
|---|---|---|---|
| 3,203,908 | 8/1965 | Kitasaki et al. | 260/665 G |
| 3,285,855 | 11/1966 | Dexter et al. | 524/291 |
| 3,422,059 | 1/1969 | Taylor et al. | 524/291 |
| 3,825,629 | 7/1974 | Hofer et al. | 524/126 |
| 3,954,847 | 5/1976 | Hofer et al. | 524/126 |
| 4,075,163 | 2/1978 | Hofer et al. | 558/162 |
| 4,187,212 | 2/1980 | Zinke et al. | 524/311 |
| 4,739,000 | 4/1988 | Burton | 524/128 |

FOREIGN PATENT DOCUMENTS

| | | | |
|---|---|---|---|
| 581938 | 8/1959 | Canada | 260/665 G |
| 1084263 | 6/1960 | Fed. Rep. of Germany | 558/144 |

OTHER PUBLICATIONS

Kazakov et al.: Sint. Metody, Osn. Elementoorg. Soedin 1982.
CA 79 (1973) 73428h.
K. Sasse, Houben-Weyl, Metboden der organischen Chemie XII/1.
Kirk-Othmer Encyclopedia of Chemical Technology, vol. 20, pp. 773-781 (1969).

*Primary Examiner*—Veronica P. Hoke

[57] ABSTRACT

A process for the preparation of organophosphorus derivatives of 2,4-di-tert-butylphenol with a high proportion of organophosphorus derivatives of biphenyl, which comprises reacting, in a first step, a 4,4'-dihalobiphenyl whose halogen has an atomic weight of at least 35, under Grignard conditions with magnesium to form the corresponding Grignard compound and this is further reacted in a second step with bis(2,4-di-tert-butylphenyl) chlorophosphite with the formation of a mixture in which at least 50% by weight of the phosphorus is combined in the form of tetrakis(2,4-di-tert-butylphenyl) 4,4'-biphenylenediphosphonite. The invention further relates to a polyolefin molding composition containing tetrakis(2,4-di-tert-butylphenyl) 4,4'-biphenylenediphosphonite which was prepared by reaction of a 4,4'-dihalobiphenyl whose halogen has an atomic weight of at least 35 with magnesium to form the Grignard compound and by subsequent reaction with bis(2,4-di-tert-butylphenyl) chlorophosphite. The invention furthermore relates to a process for the preparation of 4,4'-dihalomagnesium compounds of biphenyl by reacting a 4,4'-dihalobiphenyl whose halogen has an atomic weight of at least 35 in the absence of an entrainer, with fine-particle magnesium which is held in suspension.

19 Claims, No Drawings

PROCESS FOR THE PREPARATION OF ORGANOPHOSPHORUS DERIVATIVES OF 2,4-DI-TERT-BUTYLPHENOL, OF 4,4'-DIHALOMAGNESIUM COMPOUNDS OF BIPHENYL AND THE USE OF THE ORGANOPHOSPHORUS DERIVATIVES FOR THE STABILIZATION OF POLYOLEFIN MOLDING

DESCRIPTION

The present invention relates to a process for the preparation of organophosphorus derivatives of 2,4-di-tert-butylphenol with a high proportion of tetrakis(2,4-di-tert-butylphenyl) 4,4'-biphenylenediphosphonite, their use—optionally combined with a phenolic antioxidant—for the stabilization of plastics, in particular of polyolefins and also to a process for the preparation of 4,4'-dihalomagnesium compounds of biphenyl.

It is known that synthetic polymers must be protected from undesirable oxidative, thermal and photochemical damage during preparation, processing and use, by stabilizers or stabilizer systems. Stabilizers of this type are composed for example of a phenolic antioxidant, which is intended in particular to ensure the long term stability in use of the finished article, and one or more costabilizers, which control the processing stability and to some extent also synergistically reinforce the action of the phenolic component.

A known stabilizer combination of this type is composed of a phenolic antioxidant with a symmetrical triaryl phosphite of the formula V (cf. formula sheet) in which the radical $R^1$ is tert-butyl, 1,1-dimethylpropyl, cyclohexyl or phenyl, one of the radicals $R^2$ and $R^3$ is hydrogen and the other hydrogen, methyl or one of the radicals defined under $R^1$ (cf. DE-A-2,606,358=U.S. Pat. No. 4,187,212). In particular, tris(2,4-di-tert-butylphenyl) phosphite, together with a phenolic antioxidant, is frequently used in practice. These frequently used stabilizers are, however, not suitable for all applications.

It is also known to use benzenephosphonic acid compounds of the formula VI (cf. formula sheet) in which n=1 or 2 and $X_1$ and $X_2$ are inter alia phosphonic ester groups which may contain alkylphenyl radicals for the stabilization of plastics against degradation by light, oxygen and heat (cf. DE-A-2,152,481=U.S. Pat. No. 3,825,629). Known compounds of this type include tetrakis(2,4-di-tert-butylphenyl) 4,4'-biphenylenediphosphonite of the formula I (cf. formula sheet) whose preparation is described in those publications in Example 12. However, the effectiveness of the commercially available compound is still inadequate.

Until now, compound I has been obtained industrially in a two-step process. In the first step, biphenyl is reacted with at least twice the molar amount of phosphorus trichloride and aluminum(III) chloride, the reaction product is then complexed with $POCl_3$ and after separating off the $AlCl_3$—$POCl_3$ complex the tetrachloro-4,4'-biphenylenediphosphonite is obtained. This intermediate is converted in the second step by further reaction with corresponding amounts of 2,4-di-tert-butylphenol into product I, the hydrogen chloride liberated being neutralized by a suitable base.

In this known process, compound I results together with other reaction products, so that only less than 50% of the phosphorus, determined by $^{31}$P-NMR analysis, is combined in the form of compound I. The mixture thus obtained, from which compound I obviously does not, need to be isolated for industrial use, contains five phosphorus-containing main components in addition to phosphorus-free components:

| $^{31}$P-NMR | chem. shift | % of total P | Assignment to the formula |
|---|---|---|---|
| (CDCl$_3$): | δ = 154.7 ppm | 12.7 | I |
| | = 154.5 ppm | 12.0 | |
| | = 154.2 ppm | 46.0 | |
| | = 153.5 ppm | 15.1 | |
| | = 129.8 ppm | 13.7 | |

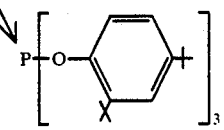

One of the significant disadvantages of this process is that, relative to the target compound I, the inevitable production of two equivalents of the $AlCl_3$—$POCl_3$ complex has to be tolerated. The disposal of this waste material is expensive. Novel processes for the preparation of compound I which do not have disadvantages of this type are therefore very desirable.

Surprisingly, it has now been found that the diphosphonite of the formula I can be prepared in a simple and advantageous manner and also in higher purity by initially reacting, in a first step, a 4,4'-dihalobiphenyl (II) whose halogen has an atomic weight of at least 35 and is preferably however chlorine or bromine, under Grignard conditions, i.e. advantageously under conditions of very thorough mixing, with magnesium to form the corresponding Grignard compound, the 4,4'-dihalomagnesiumbiphenyl III, and this is further reacted in a second step with bis(2,4-di-tert-butylphenyl) chlorophosphite of the formula IV (cf. claim 1) with the formation of a mixture in which at least 50% by weight of the phosphorus is combined in the form of tetrakis(2,4-di-tert-butylphenyl) 4,4'-biphenylenediphosphonite of the formula I (cf. claim 1), the bonding of the phosphorus being determined by $^{31}$P-NMR analysis.

It is known from the literature that direct Grignardization of dihalobiphenylene results only in an unsatisfactory yield of the dihalomagnesiumbiphenylene III. In this reaction, in order to achieve acceptable yields, it is normal to use "entrainers" such as ethyl bromide and auxiliaries such as hexamethylphosphoric triamide whose use is undesirable for toxicological reasons [Kazakov et al., Sint. Metody. Osn. Elementoorg. Soedin. 1982, 3–6].

In one embodiment of the present invention, it is then preferable in the first step of the process according to the invention, which can be carried out by any normal procedure for preparing the 4,4'-dihalomagnesiumbiphenyls III in the absence of an entrainer, to operate in such a way that the dihalobiphenyls (II) are reacted directly with at least two equivalents of magnesium to form the Grignard compound III, the magnesium being held in suspension by intimate mixing. The reaction can be accelerated and the degree of conversion improved if a slight excess of magnesium is used. It is advantageous to use 2.2 to 3 equivalents of magnesium per mole of dihalobiphenyl. The suspension is preferably maintained by vortexing in particular by using ultrasound.

The ultrasound can be produced by a generator which is arranged inside or outside the reaction vessel.

The reaction in the first step is preferably carried out in an aprotic, organic solvent such as an ether, for example diethyl ether, dipropyl ether or diisopropyl ether, ethylene glycol dimethyl ether or ethylene glycol diethyl ether, diethylene glycol dimethyl ether or diethylene glycol diethyl ether, methyl tert-butyl ether, dioxane or tetrahydrofuran.

Since the intermediates III are sensitive to hydrolysis and oxidation, it can be advantageous to operate under an inert gas atmosphere. Particularly suitable inert gases are nitrogen and argon.

The reaction temperature is generally between 20° and 125° C., preferably between 30° and 70° C. The duration of the reaction can be varied within wide limits and depending on the temperature and size of the batch is generally 2 to 24 hours.

Particular preference is given in every case to the use of 4,4'-dibromobiphenyl among the 4,4'-dihalobiphenyls II.

In order to react further to form the phosphonite I, the Grignard compound III is metered into the phosphoric diester chloride IV which is advantageously diluted with an inert aprotic solvent, for example hexane, toluene, xylene or one of the ethers given above. The reactants in this step are generally added together slowly at between −30° C. and +30° C., preferably however between −20° C. and 20° C. The reaction is weakly exothermic; it can therefore be advantageous to control the course of the reaction by cooling. The most favorable results are obtained if the reactants are used in stoichiometric amounts. However, it is also possible to use one reactant in excess; but in general there are no particular advantages in doing so. It is advantageous to stir the system until the reaction has ended, which can be hastened by heating to 0° to 30° C., and to separate off the precipitated magnesium halide. The solvent can be removed from the filtrate in a customary manner, preferably by distillation, particularly under reduced pressure.

The ester chloride IV is readily accessible from phosphorus trichloride and 2,4-di-tert-butylphenol (U.S. Pat. No. 4,739,000). The purity of the starting material obtained by this method is about 85-90% (according to $^{31}$P-NMR).

The compound I can be isolated from the crude product by any desired process.

Since ester groups which are bonded to the phosphorus atom behave toward organometallic compounds essentially like halogen atoms (K. Sasse, Houben-Weyl, Methoden der org. Chemie XII/1, 44), it is particularly surprising that the phosphonite I prepared in the process according to the invention has a higher purity than that prepared in the known process. Normally, it would be expected that when highly reactive, difunctional Grignard compounds are used, the yield is diminished by substantial side reactions. The process according to the invention has thus made it possible to obtain a product in the second step containing at least 60% of the phosphorus combined in the form of tetrakis(2,4-di-tert-butylphenyl) 4,4'-biphenylenediphosphonite.

It was subsequently found that the mixture of organophosphorus derivatives of 2,4-di-tert-butylphenol obtained according to the invention is eminently suitable, on its own or in combination with a phenolic antioxidant or other antioxidant, for the stabilization of plastics, in particular polyolefins, and imparts an improved stability against degradation by light, oxygen and heat to these plastics. This application does not require isolation of the tetrakis(2,4-di-tert-butylphenyl) 4,4'-biphenylenediphosphonite in pure form.

The invention therefore also relates to a polyolefin molding composition containing an olefin polymer and tetrakis(2,4-di-tert-butylphenyl) 4,4'-biphenylenediphosphonite in the ratio of (90 to 99.99):(0.01 to 10)% by weight, where the phosphonite has been prepared by reacting a 4,4'-dihalobiphenyl whose halogen has an atomic weight of at least 35 with magnesium to form a Grignard compound and then reacted with bis(2,4-di-tert-butylphenyl) chlorophosphite. The proportion of the polyolefin is preferably 98 to 99.95% by weight. Polypropylene is preferred.

The polyolefin in the molding composition according to the invention may for example by one of the following polymers:

1. Polymers of monoolefins or diolefins, for example polyethylene (which may be crosslinked), polypropylene, polyisobutylene, polybut-1-ene, polymethylpent-1-ene, polyisoprene or polybutadiene and also polymers of cycloolefins such as cyclopentene or norbornene.
2. Mixtures of the polymers listed in 1., for example mixtures of polypropylene with polyisobutylene.
3. Copolymers of monoolefins and diolefins with each other or with other vinyl monomers such as ethylene-propylene copolymers, propylene-but-1-ene copolymers, propylene-isobutylene copolymers, ethylene-but-1-ene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene acrylic acid copolymers and salts thereof (ionomers), and also terpolymers of ethylene with propylene and a diene such as hexadiene, dicyclopentadiene or ethylidenenorbornene.

The phenolic antioxidant is for example an ester of 3,3-bis(3'-tert-butyl-4'-hydroxyphenyl)butanoic acid of the formula VII (cf. formula sheet) in which n is 1 or 2 and $R^4$ denotes a $C_1$-$C_{12}$-alkyl radical if n is 1, and a $C_1$-$C_{12}$-alkylene radical if n is 2. $R^4$ is preferably a $C_2$-$C_4$-alkylene radical, in particular a $C_2$-alkylene radical.

However, the phenolic antioxidant may also be an ester of β-(3,5-di-tert-butyl-4-hydroxyphenyl)propionic acid of the formula VIII (cf. formula sheet), where the alcohol component is a monohydric to tetrahydric alcohol such as methanol, octadecanol, 1,6-hexanediol, neopentyl glycol, diethylene glycol, triethylene glycol, pentaerythritol, tris-hydroxyethyl isocyanurate, thiodiethylene glycol or di-hydroxyethyl-oxamide.

The proportion of the phosphonite and optionally of the phenolic antioxidant in the molding composition according to the invention is advantageously 0.01 to 5, preferably 0.025 to 1% by weight for the phosphonite and 0.01 to 5, preferably 0.025 to 1% by weight for the phenolic antioxidant.

The molding composition according to the invention can additionally contain other antioxidants such as:

1. Alkylated monophenols, for example 2,6-di-tert-butyl-4-methylphenol, -4-ethylphenol, -4-n-butylphenol, -4-iso-butylphenol, 2-tert-butyl-4,6-dimethylphenol, 2,6-di-cyclopentyl-4-methylphenol, 2-(α-methylcyclohexyl)-4,6-dimethylphenol, 2,6- di-octadecyl-4-methylphenol, 2,4,6-tri-cyclohexylphenol, 2,6-di-tert-butyl-4-methoxymethylphenol;
2. Alkylated hydroquinones such as 2,5-di-tert-butyl- and 2,5-di-tert-amyl-hydroquinone, 2,6-di-tert-butyl-4-methoxyphenol and 2,6-diphenyl-4-octadecyloxyphenol;
3. 1.3 Hydroxylated thiodiphenyl ethers such as 2,2'-thio-bis(6-tert-butyl-4-methylphenol) and -(4-octylphenol) and also 4,4'-thio-bis(6-tert-butyl-3-methylphenol) and -(6-tert-butyl-2-methylphenol);
4. Alkylidene-bisphenols such as 2,2'-methylene-bis(6-tert-butyl-4-methylphenol), -(6-tert-butyl-4-ethylphenol), [4-methyl-6-(α-methylcyclohexyl)-phenol], -(4-methyl-6-cyclohexylphenol), -(6-nonyl-4-methylphenol), -(4,6-di-tert-butylphenol), -[6-(α-methylbenzyl)-4-nonylphenol], -[6-(α,α-dimethylbenzyl)-4-nonylphenol], 4,4'-methylene-bis(2,6-di-tert-butylphenol) and -(6-tert-butyl-2-methylphenol), 2,2'-ethylidene-bis(4,6-di-tert-butylphenol) and -(6-tert-butyl-4-isobutylphenol), 1,1-bis- and 1,1,3-tris(5-tert-butyl-4-hydroxy-2-methylphenyl)butane, 2,6-di-(3-tert-butyl-5-methyl-2-hydroxybenzyl)-4-methylphenol, 1,1-bis(5-tert-butyl-4-hydroxy-2-methylphenyl)-3-n-dodecylmercaptobutane, di-(3-tert-butyl-4-hydroxy-5-methylphenyl)dicyclopentadiene;
5. Benzyl compounds such as di-[2-(3'-tert-butyl-2'-hydroxy-5'-methyl-benzyl)-6-tert-butyl-4-methylphenyl] terephthalate, 1,3,5-tri(3,5-di-tert-butyl-4-hydroxybenzyl)-2,4,6-trimethylbenzene, di-(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl)dithiol terephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate and the calcium salt of monoethyl 3,5-di-tert-butyl-4-hydroxybenzylphosphonate;
6. Acylaminophenols such as 4-hydroxylauranilide and 4-hydroxystearanilide, 2,4-bis-octylmercapto-6-(3,5-di-tert-butyl-4-hydroxyanilino)-s-triazine and octyl N-(3,5-di-tert-butyl-4-hydroxyphenyl)-carbamate;
7. Esters of β-(5-tert-butyl-4-hydroxy-3-methylphenyl)propionic acid with monohydric or polyhydric alcohols such as methanol, octadecanol, 1,6-hexanediol, neopentyl glycol, diethylene glycol, triethylene glycol, pentaerythritol, tris-hydroxyethyl isocyanurate, thiodiethylene glycol or di-hydroxyethyl-oxamide;
8. Amides of β-(3,5-di-tert-butyl-4-hydroxyphenyl)-propionic acid, such as N,N'-di-(3,5-di-tert-butyl-4-hydroxyphenylpropionyl)trimethylenediamine, -hexamethylenediamine and -hydrazine.

Furthermore, the molding composition according to the invention may contain other additives such as:
1. UV absorbers and light stabilizers, for example
1.1 2-(2'-Hydroxymethyl)benzotriazoles, such as the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl, 3',5'-bis(α,α-dimethylbenzyl) derivative;
1.2 2-Hydroxybenzophenones, such as the 4-hydroxy-, 4-methoxy, 4-octoxy, 4-decyloxy, 4-dodecyloxy, 4-benzyloxy, 4,2',4'-trihydroxy, 2'-hydroxy-4,4'-dimethoxy derivative;

1.3 Esters of optionally substituted benzoic acids, such as phenyl salicylate, 4-tert-butylphenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate.
1.4 Acrylates, such as ethyl and iso-octyl α-cyano-β,β-diphenyl acrylate, methyl α-carbomethoxycinnamate and methyl α-carbomethoxy-p-methoxycinnamate, methyl α-cyano-β-methyl-p-methoxycinnamate and butyl α-cyano-β-methyl-p-methoxycinnamate, N-(β-carbomethoxy-β-cyanovinyl)-2-methylindoline;
1.5 Nickel compounds, such as nickel complexes of 2,2'-thio-bis[4-(1,1,3,3-tetramethyl-butyl)phenol], such as the 1:1 or 1:2 complex, optionally with additional ligands such as n-butylamine, triethanolamine or N-cyclohexyldiethanolamine, nickel alkyl dithiocarbamates, nickel salts of monoalkyl 4-hydroxy-3,5-di-tert-butylbenzylphosphonates such as the methyl or ethyl ester, nickel complexes of ketoximes such as those of 2-hydroxy-4-methylphenyl undecyl ketoxime, nickel complexes of 1-phenyl-4-lauroyl-5-hydroxypyrazole, optionally with additional ligands;
1.6 Sterically hindered amines, such as bis(2,2,6,6-tetramethylpiperidyl) sebacate, glutarate and succinate, bis(1,2,2,6,6-pentamethylpiperidyl) sebacate, glutarate and succinate, 4-stearyloxypiperidine and 4-stearoyloxy-2,2,6,6-tetramethylpiperidine, 4-stearoyloxy-1,2,2,6,6-pentamethylpiperidine, bis(1,2,2,6,6-pentamethylpiperidyl) n-butyl-3,5-di-tert-butyl-4-hydroxybenzylmalonate, the condensation product from 1-hydroxymethyl-2,2,6,6-tetramethyl-4-hydroxypiperidine and succinic acid, the condensation product from N,N'-(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetracarboxylic acid, 1,1'-(1,2-ethanediyl)-bis(3,3,5,5-tetramethylpiperazinone);
1.7 Oxamides, such as 4,4'-di-octyloxyoxanilide, 2,2'-di-octyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and the mixture thereof with 2-ethoxy-2'-ethyl-5,4-di-tert-butyloxanilide, mixtures of o- and p-methoxy- and -ethoxy-di-substituted oxanilides;
2. Metal deactivators, such as N,N'-diphenyloxamide, N-salicylyl-N'-salicyloylhydrazine, N,N'-bissalicyloylhydrazine, N,N'-bis(3,5-di-tert-butyl-4-hydroxyphenylpropionyl)hydrazine, 3-salicyloylamino-1,2,3-triazole, bis-benzylideneoxalic acid dihydrazide;
3. Peroxide-destroying compounds, such as esters of β-thiodipropionic acid, for example the lauryl, stearyl, myristyl or tridecyl esters, mercaptobenzimidazole, the zinc salt of 2-mercaptobenzimidazole, zincalkyl dithiocarbamates, dioctadecyl sulfide, pentaerythritol tetrakis(β-dodecylmercapto)propionate;
4. Basic co-stabilizers, such as melamine, polyvinylpyrrolidone, dicyanodiamide, triallyl cyanurate, urea derivatives, hydrazine derivatives, amines, polyamines, polyurethanes, alkali metal salts and alkaline earth metal salts of higher fatty acids or phenolates, for example Ca stearate, Zn stearate and Mg stearate, Na ricinoleate, K palmitate, antimony catecholate or tin catecholate, hydroxides and oxides of alkaline earth metals or of aluminum, for example CaO, MgO, ZnO;

5. Nucleating agents, such as 4-tert-butylbenzoic acid, adipic acid, diphenylacetic acid;
6. Fillers and reinforcing agents, such as calcium carbonate, silicates, glass fibers, asbestos, talc, kaolin, mica, barium sulfate, metal oxides and hydroxides, carbon black, and graphite;
7. Other additives, such as plasticizers, lubricants, emulsifiers, pigments, optical brighteners, flame retardants, antistatic agents, blowing agents.

The preparation of the polyolefin molding composition according to the invention is carried out by customary methods. It can for example be carried out by incorporating the stabilizers and optionally other additives by the processes customary in the technology either before or during shaping, or else by applying the dissolved or dispersed compounds to the polymer, optionally with subsequent evaporation of the solvent or dispersing agent. The stabilizers can also be added in the form of a masterbatch which can contain these products in a concentration of about 2.5 to 25% by weight, which is added to the molding composition to be prepared. It is also possible to make the addition prior to any crosslinking.

The various additional additives of the above groups 1 to 5 are generally added to the molding composition according to the invention in an amount of from 0.01 to 10, preferably 0.01 to 5% by weight, relative to the total weight of the molding composition. The proportion of the additives from groups 6 and 7 is generally 1 to 80, preferably 10 to 50% by weight, relative to the total molding composition.

The invention is described in more detail using the following examples:

I Examples of preparation 1 and 2—Preparation of the dihalomagnesium compounds

1) The solution of 70.2 g (=0.225 mole) of 4,4'-dibromobiphenyl in 180 ml of tetrahydrofuran was heated at 50° C. with 10.93 g (=0.45 mole) of Mg shavings with the addition of catalytic amounts of iodine under an atmosphere of nitrogen and with the exclusion of moisture until the beginning of the Grignardization. After the weakly exothermic reaction had receded, the suspension was diluted with 150 ml of tetrahydrofuran and agitated at 60° C. in an ultrasound bath (40 kHz frequency) until the magnesium had dissolved.

2) The procedure of Example 1 was repeated except that 14.2 g (=0.58 mole) of magnesium shavings were used. Agitation was carried out for 5 hours in an ultrasound bath at 60° C.

3 and 4—Preparation of the organophosphorus derivatives

3) The greenish Grignard suspension obtained according to Example 1 was metered with vigorous stirring at a temperature of −15° C. to −5° C. into the solution of 214.7 g (=0.45 mole) of bis(2,4-di-tert-butylphenyl) chlorophosphite in 250 ml of tetrahydrofuran. After removing the cooling, the mixture was stirred for a further 2½ hours at room temperature and the Mg salt filtered off. After distilling off the solvent under reduced pressure, a brittle material remained which was pulverized and further dried under reduced pressure (yield 223 g). 63% of the phosphorus was combined in the form of tetrakis (2,4-di-tert-butylphenyl) 4,4'-biphenylenediphosphonite.

4) The procedure of Example 3 was followed except that 250 ml of a mixture of tetrahydrofuran and hexane (ratio by volume 2:1) were used as the solvent, and the Grignard suspension obtained according to Example 2 was metered in. About 220 g of a beige powder were obtained, with a softening point of 75°–77° C., in which 70% of the phosphorus was combined in the form of tetrakis(2,4-di-tert-butylphenyl) 4,4'-biphenylenediphosphonite.

II Examples of use

The tetrakis(2,4-di-tert-butylphenyl) 4,4'-biphenylenediphosphonite used in Example 5 and 6 was obtained by the method described in Example 3.

The tetrakis(2,4-di-tert-butylphenyl) 4,4'-biphenylenediphosphonite used in the Comparative Examples D and E was obtained as disclosed in DE-A-2,152,481, wherein in the first step biphenyl was reacted with at least twice the molar amount of phosphorus trichloride and aluminum-(III) chloride, the reaction product was then complexed with $POCl_3$ and after separating off the $AlCl_3$—$POCl_3$ complex, the tetrachloro-4,4'-biphenylenediphosphonite was obtained. This intermediate was converted in the second step by further reaction with corresponding amounts of 2,4-di-tert-butylphenol to form the desired phosphonite and the hydrogen chloride liberated was neutralized using a suitable base.

5 and 6 and Comparative Examples A to E 100.0 g of unstabilized polypropylene powder (density: 0.903 g/cm$^3$; melt flow index MFI 230/5: 4 g/10 min) were mixed with 0.1 g of Ca stearate as acid acceptor and 0.05 g of ethylene glycol bis(3,3-bis(3'-tert-butyl-4'-hydroxyphenyl)butyrate and the amounts of phosphorus compound listed in the tables and repeatedly extruded using a laboratory extruder (short compression zone screw, screw diameter 20 mm; length 400 mm; die 30 mm in length; 2 mm in diameter; screw rotational speed: 125 rpm; temperature profile: 200°/230°/230° C.). After the 1st, 5th and 10th pass, samples of the granules were taken and subjected to measurement of the melt flow index (MFI) in accordance with DIN 53 735 and also of the yellowing as the yellowness index in accordance with ASTM D 1925-70.

The results are listed in Tables 1 and 2.

The phosphonite which is to be used according to the invention maintains the melt viscosity of the molding composition at the highest level (lowest melt flow index and with the highest consistency. This phosphonite moreover produces the best initial colors in the test samples and the least color change after 10-fold granulation.

TABLE 1

Effect of phosphorus compounds on the processing stability of polypropylene Melt flow index MFI 230/5 after repeated granulation. (MFI in g/10 min)

| Example | Phosphorus compound | MFI after 1st | 5th | 10th granulation |
|---|---|---|---|---|
| Comp. A | none | 8.0 | 12.7 | 17.5 |
| Comp. B | 0.05 g tris(2,4-di-tert-butyl-phenyl) phosphite | 6.7 | 7.5 | 10.5 |
| Comp. C | 0.10 g tris(2,4-di-tert-butyl-phenyl) phosphite | 5.5 | 6.1 | 7.4 |
| Comp. D | 0.05 g commercially available phosphonite* | 5.7 | 6.1 | 6.7 |
| Comp. E | 0.10 g commercially available phosphonite* | 5.0 | 5.6 | 6.4 |
| 5 | 0.05 g phosphonite* according to the invention | 6.0 | 5.8 | 5.8 |
| 6 | 0.10 g phosphonite* according to the invention | 4.9 | 4.8 | 5.6 |

*tetrakis(2,4-di-tert-butylphenyl) 4,4'-biphenylenediphosphonite

TABLE 2

Yellowing (yellowness index in accordance with ASTM D 1925-70) with repeated granulation of polypropylene.

| Example | Phosphorus compound | Yellowness index after the 1st | 5th | 10th granulation |
|---|---|---|---|---|
| Comp. A | none | 8.9 | 13.4 | 19.3 |
| Comp. B | 0.05 g tris(2,4-di-tert-butyl-phenyl) phosphite | 9.0 | 18.8 | 32.3 |
| Comp. C | 0.1 g tris(2,4-di-tert-butyl-phenyl) phosphite | 8.1 | 13.1 | 26.6 |
| Comp. D | 0.05 g commercially available phosphonite* | 4.7 | 6.6 | 11.3 |
| Comp. E | 0.1 g commercially available phosphonite* | 4.7 | 6.1 | 9.5 |
| 5 | 0.05 g phosphonite* according to the invention | 5.9 | 6.8 | 10.1 |
| 6 | 0.1 g phosphonite* according to the invention | 5.3 | 5.6 | 7.8 |

*tetrakis(2,4-di-tert-butylphenyl) 4,4'-biphenylenediphosphonite

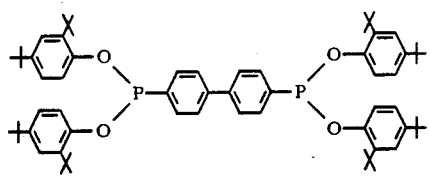

I

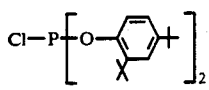

IV

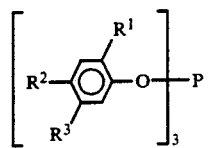

V

VI

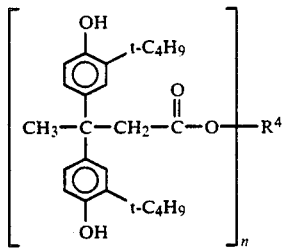

VII

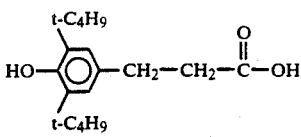

VIII

We claim:
1. A process for the preparation of 4,4'-dihalomagnesium compounds of biphenyl, which comprises reacting a 4,4'-dihalobiphenyl in which the halogen has an atomic weight of at least 35, in the absence of an entrainer under Grignard-conditions with finely divided magnesium which is held in fine suspension by ultrasonic action.
2. A process as claimed in claim 1, wherein 4,4'-dichlorobiphenyl or 4,4'-dibromobiphenyl is reacted.
3. A process as claimed in claim 1, wherein 2.2 to 3 equivalents of magnesium are reacted per mole of dihalobiphenyl.

4. Process for the preparation of phosphororganic derivatives of 2,4-di-t.-butylphenol, which comprises reacting in a first stage a 4,4'-dihalobiphenyl in which the halogen has an atomic weight of at least 35, in the absence of an entrainer under Grignard-conditions with finely divided magnesium which is held in suspension by ultrasonic action, to yield the corresponding Grignard-compound, and reacting this compound in a second stage with the chloride of phosphorous acid-bis-(2,4-di-t.-butylphenyl)ester of the formula IV

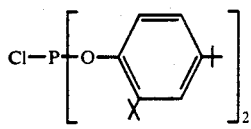

to yield a composition in which at least 50% by weight of the phosphorus are bound in the form of tetrakis-(2,4-di-t.-butyl-phenyl)-4,4'-biphenylene-diphosphonite of the formula I

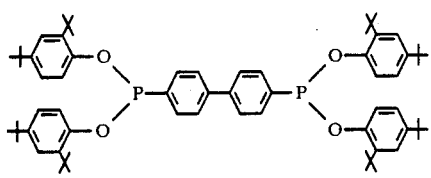

the nature of the bonding of the phosphorus being determined by $^{31}$P-NMR-analysis.

5. A process as claimed in claim 4, wherein 2.2 to 3 equivalents of magnesium are reacted per mole of dihalobiphenyl.

6. Process for the preparation of phosphoroganic derivatives of 2,4-di-t.-butylphenol, which comprises reacting in a first stage a 4,4'-dihalobiphenyl in which the halogen has an atomic weight of at least 35, in the absence of an entrainer under Grignard-conditions with finely divided magnesium which is held in suspension by vortexing, to yield the corresponding Grignard-compound and reacting this compound in a second stage with the chloride of phosphorous acid-bis-(2,4-di-t.-butylphenyl)-ester of the formula IV

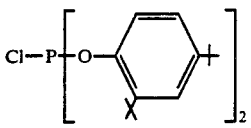

to yield a composition in which at least 50% by weight of the phosphorus are bound in the form of tetrakis-(2,4-di-t.-butyl-phenyl)-4,4'-biphenylene-diphosphonite of the formula I

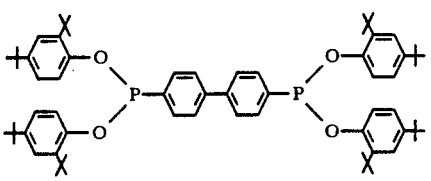

the nature of the bonding of the phosphorus being determined by $^{31}$P-NMR-analysis.

7. A process as claimed in claim 6, wherein in the final reaction product at least 60% of the phosphorus are bound in the form of tetrakis-(2,4-di-t.-butyl-phenyl)-4,4'-biphenylene-diphosphonite.

8. A process as claimed in claim 6, wherein the second stage is carried out at a temperature in the range of from $-30°$ to $+30°$ C.

9. A process as claimed in claim 8, wherein the second stage is carried out at a temperature in the range of from $-20°$ to $+20°$ C.

10. A process as claimed in claim 6, wherein a 4,4'-dichlorobiphenyl or a 4,4'-dibromobiphenyl is reacted.

11. A process as claimed in claim 6, wherein the amount of said finely divided magnesium is 2.2 to 3 equivalents per mole of said 4,4'-dihalobiphenyl.

12. A process as claimed in claim 6 wherein the vortexing is effected by ultrasonic action, and the amount of said finely divided magnesium is at least two equivalents per mole of said 4,4'-dihalobiphenyl.

13. A process for the preparation of 4,4'-dihalomagnesium compounds of biphenyl, which comprises reacting a 4,4'-dihalobiphenyl in which the halogen has an atomic weight of at least 35, in the absence of an entrainer under Grignard conditions with finely divided magnesium which is held in fine suspension by vortexing.

14. A process as claimed in claim 13 wherein 2.2 to 3 equivalents of magnesium are reacted per mole of 4,4'-dihalobiphenyl, and the vortexing is effected by ultrasonic action.

15. A process for stabilizing a polyolefin molding composition comprising 90 to 99.99% by weight of an olefin polymer which comprises effecting the stabilization of said composition with 0.01 to 10% by weight of tetrakis-(2,4-di-t.-butyl-phenyl)-4,4'-biphenylene-diphosphonite having been obtained in accordance with claim 6.

16. A process as claimed in claim 15 wherein said composition comprises
90% to 99.98% by weight of an olefin polymer,
0.01% to 5% by weight of the tetrakis-(2,4-di-t.-butylphenyl)-4,4'-biphenylene-diphosphonite
0.01% to 5% by weight of an ester of 3,3-bis-(3'-t.-butyl-4'-hydroxyphenyl)-butanic acid of the formula VII

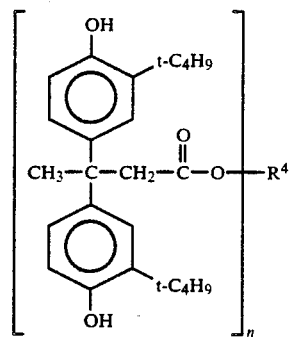

wherein n is 1 or 2 and $R^4$ represents a $C_1$–$C_{12}$-alkyl group, if n is 1, or $R^4$ represents a $C_1$–$C_{12}$-alkylene group, if n is 2, or an ester of $\beta$-(3,5-di-t.-butyl-4-hydroxyphenyl)-propionic acid of the formula VIII

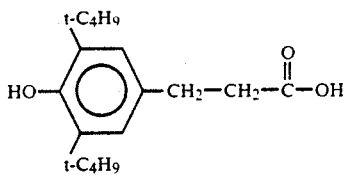

with an at most tetrahydic alcohol.

17. A process as claimed in claim 15, wherein the polyolefin is polypropylene.

18. The process as claimed in claim 15, wherein the second stage reaction product has at least 60% of the phosphorus being bound in the form of said tetrakis-(2,4-di-t.-butyl-phenyl)-4,4'-biphenylene-diphosphonite.

19. The process as claimed in claim 16, wherein the second stage reaction product has at least 60% of the phosphorus being bound in the form of said tetrakis-(2,4-di-t.-butylphenyl)-4,4'-biphenylene-diphosphonite.

* * * * *